United States Patent
Fontana et al.

(10) Patent No.: US 8,193,210 B2
(45) Date of Patent: Jun. 5, 2012

(54) CAMPTOTHECIN DERIVATIVES WITH ANTITUMOR ACTIVITY

(75) Inventors: Gabriele Fontana, Milan (IT); Ezio Bombardelli, Gropello Cairoli (IT); Carla Manzotti, Milan (IT); Arturo Battaglia, Bologna (IT); Maria Grazia Allegri, legal representative, Bologna (IT); Cristian Samori, Forli' (IT)

(73) Assignee: Indena S.p.A., Milan (IT)

( * ) Notice: Subject to any disclaimer, the term of this patent is extended or adjusted under 35 U.S.C. 154(b) by 562 days.

(21) Appl. No.: 12/373,834

(22) PCT Filed: Jul. 16, 2007

(86) PCT No.: PCT/EP2007/006294
§ 371 (c)(1),
(2), (4) Date: Jun. 26, 2009

(87) PCT Pub. No.: WO2008/012003
PCT Pub. Date: Jan. 31, 2008

(65) Prior Publication Data
US 2010/0010032 A1    Jan. 14, 2010

(30) Foreign Application Priority Data
Jul. 26, 2006    (IT) ............................... MI2006A1474

(51) Int. Cl.
*A61K 31/4745*    (2006.01)
*C07D 491/22*    (2006.01)
(52) U.S. Cl. .......................................... 514/283; 546/48
(58) Field of Classification Search .................. 514/283; 546/48
See application file for complete search history.

(56) References Cited

U.S. PATENT DOCUMENTS
5,972,955 A    10/1999    Duvvuri et al.

OTHER PUBLICATIONS

Brunin et al.; "Towards new camptothecins. Part 3: Synthesis of 5-methoxycarbonyl camptothecin", Tetrahedron, Elsevier Science Publishers, Apr. 24, 2006, pp. 3959-3968, vol. 62, No. 17, Amsterdam, NL.
Subrahmanyam et al., "Novel C-ring analogues of 20(s)-camptothecin. Part 3: synthesis and their in vitro cytotoxicity of A-, B- and C-ring analogues", Bioorganic & Medicinal Chemistry Letters, Feb. 4, 2000, vol. 10, No. 4, Oxford, GB.

*Primary Examiner* — Charanjit Aulakh
(74) *Attorney, Agent, or Firm* — Arent Fox LLP

(57) ABSTRACT

Novel camptothecin derivatives having antitumor activity, the processes for the preparation thereof, the use thereof as antitumor drugs and pharmaceutical compositions containing them.

11 Claims, No Drawings

CAMPTOTHECIN DERIVATIVES WITH ANTITUMOR ACTIVITY

CROSS-REFERENCE TO RELATED APPLICATION

This application is a National Stage entry of International Application No. PCT/EP2007/006294, filed Jul. 16, 2007, the entire specification and claims of which are incorporated herewith by reference.

The present invention relates to novel camptothecin derivatives having antitumor activity, the processes for the preparation thereof, the use thereof as antitumor drugs and pharmaceutical compositions containing them.

BACKGROUND OF THE INVENTION

Camptothecin is an alkaloid extracted from *Camptotheca acuminata* (Nyssaceae), first described by Wall and Wani in 1966 (J. Am. Chem. Soc. 1966, 88, 3888-3890). Camptothecin, albeit endowed with wide spectrum antitumor activity, especially against colon tumor and other solid tumors and leukemias, is not used in therapy due to its high toxicity, which is particularly manifested in the form of hemorrhagic cystitis, gastrointestinal toxicity and myelosuppression.

A number of camptothecin analogues have been synthesized in order to obtain compounds having low toxicity and high solubility. At present, two drugs are used in clinical practice, namely CPT-11 and topotecan. Other derivatives, such as belotecan, rubitecan, exatecan, gimatecan, pegamotecan, lurtotecan, karenitecin, afeletecan, homocamptothecin, diflomotecan, and many others, are undergoing clinical experimentation. Compound CPT-11 is a highly soluble prodrug for 10-hydroxy-7-ethylcamptothecin (commonly known as SN-38), approved for the treatment of many solid tumors and ascites (colorectal, skin, stomach, lung, cervice, ovary, non-Hodgkin lymphoma).

Topotecan is a compound soluble in physiological solution, active against the tumors of the lung, stomach, liver, ovary, breast, prostate, esophagus, rectum, soft tissues sarcomas, head and neck, glioblastoma, chronic and acute myelocytic leukemias. Topotecan shows, however, important side effects such as neutropenia and thrombocytopenia.

Lurtotecan is a more soluble derivative, having activity in tumors of the neck, ovary, breast, colo-rectal, and pulmonary microcytoma. However, Lurtotecan also has hematic toxicity.

Rubitecan is a prodrug for the oral use effective against tumors of the pancreas, ovary and breast.

Camptothecin and its analogues, as is the case with all topoisomerase I inhibitors, are effective against tumors resistant to conventional drugs, including topoisomerase II inhibitors; maintain high topoisomerase levels during the whole cell cycle; do not induce multi-drug resistance (Pgo or MRP) or detoxifying metabolism mediated by the enzyme.

Research is now focused on novel inhibitors of the topoisomerase I having lower toxicity than the presently used drugs.

Open-ring camptothecin derivatives show high protein binding (in particular with albumin) and low distribution in the tumor tissues. As a consequence, the product accumulates in the body and tumors are poorly affected.

Conversely, the high lipophilicity of the lactone form promotes the adhesion of camptothecin derivatives to cell membranes, particularly erythrocytes, affecting the tissue/plasma distribution ratio. For this reason, research is being focused towards two alternative approaches: a) design of low protein binding products still having good solubility; b) design of highly potent products having therapeutical effect even at extremely low doses.

Modifications at the 7-, 9-, 10- and 11-positions usually proved well tolerated while not affecting the stability of the DNA-Topoisomerase I-camptothecin ternary complex, the formation of which is responsible for the antitumor activity of the compounds.

Products with 20R configuration proved either inactive or very less active than the products with 20S configuration—which coincides with the natural configuration.

As a rule, modifications at the 5-position are considered unfavourable to the formation of the ternary complex, whereas modifications at the pyridone rings D and E have bee reported to be deleterious to the activity of the product.

DISCLOSURE OF THE INVENTION

In a first aspect, the invention relates to camptothecin derivatives of general formula I:

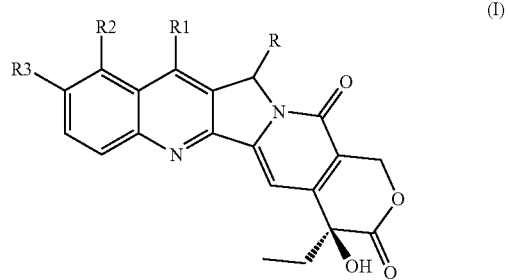

wherein:
R is F, Cl, Br, I, —N3, NH2, —NR'R", —COOR', —CONR'R", —NHR'"—NR'R" in which R', R" and R'" can be H, alkyl, aryl, arylalkyl, acyl, alkoxycarbonyl, aryloxycarbonyl;

R1 is alkyl, aminoalkyl, hydroxyalkyl, nitrile, alkoxymino, aryloxymino, silylalkyl;

R2 is hydrogen, hydroxyl, alkoxy, aminoalkyl;

R3 is hydrogen, optionally protected hydroxyl, alkoxy, aminoalkyl;

wherein the alkyl, acyl, alkoxy, aminoalkyl or alkoxymino groups can contain 1 to 8, preferably 1 to 4, carbon atoms, in a straight or branched chain, and the aryl and aryloxy groups can contain 5 to 10 carbon atoms;

the pharmaceutically acceptable salts, isomers, enantiomers, diastereomers thereof and corresponding mixtures.

The compounds of the invention show low protein binding and have good solubility and high potency even at very low doses.

The preferred synthetic route for the preparation of the compounds of the invention is illustrated in Scheme and comprises the following steps:

a) protection of the precursor hydroxy groups;

b) derivatization at 5 through formation of a carbanion and reaction with an electrophilic reagent;

c) deprotection of the hydroxy groups;

Scheme

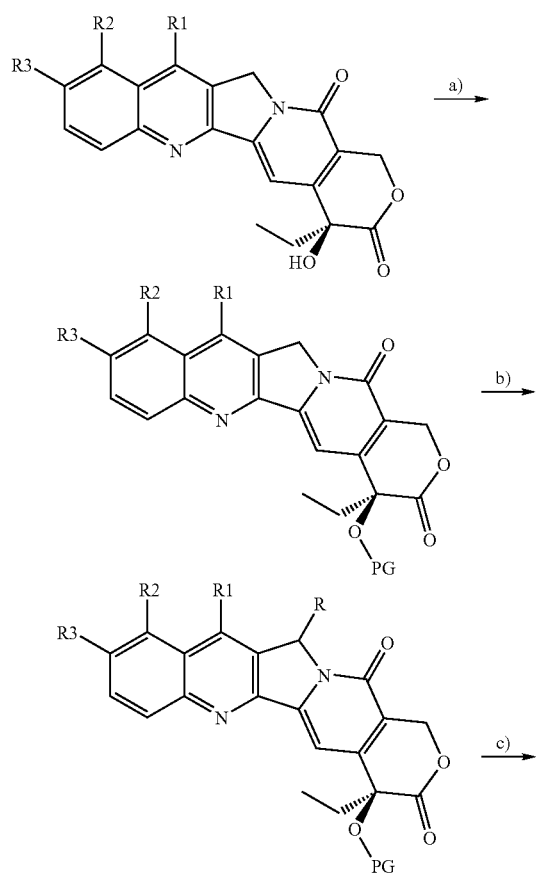

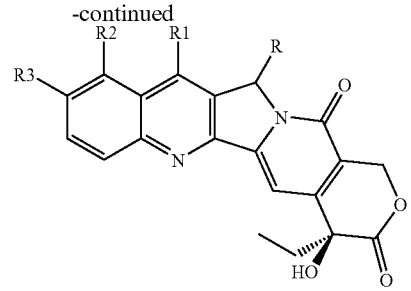

In Scheme, R, R1, R2 and R3 have the meanings described above, and PG is a hydroxy-protecting group.

Precursors may be commercially available or obtained as described in the literature.

The carbanions at 5 can be obtained by treating the precursor with a strong organic base, preferably LiHMDS.

The carbanion is reacted in situ with an electrophilic reagent, such as a source of halogen or azadicarboxylate, isocyanate, chlorocarbonyl derivative, tosylazide.

Silyls and carbamates or a combination thereof are preferred as hydroxy-protecting groups.

The compounds of the invention were tested in a cytotoxicity assay on a wide spectrum of tumour cells. By way of example, the cytotoxicity data on the NCI-H460 cell line (NSCL cancer) concerning two compounds of formula (I) are reported, using camptothecin and the drugs Topotecan and SN-38 as references:

| Name | Formula | NCI-H460 IC50 (μg/mL) Cell count |
|---|---|---|
| Camptothecin | MW = 348.36  C20H16N2O4 | 0.115 ± 0.0174 |
| Topotecan | MW = 421 | 0.63 ± 0.44 |

-continued
| Name | Formula | NCI-H460 IC50 (μg/mL) Cell count |
|---|---|---|
| SN38 | C23H23N3O5 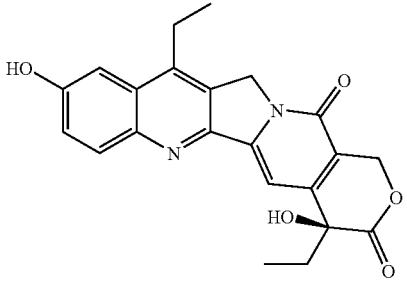 MW = 392.42 | 0.0865 ± 0.0049 |
| 5-F-camptothecin | C22H20N2O5 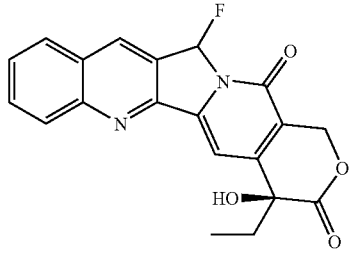 MW = 366 C20H16FN2O4 | Isomer 1: 20.6 ± 6.8 Isomer 2: 20 ± 5.1 |
| 5-N3-camptothecin | 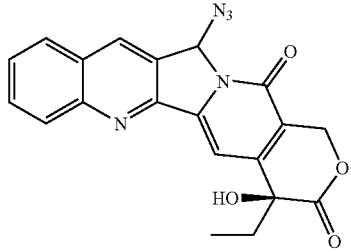 MW = 389 C20H15N5O4 | Isomer 1: 4.18 ± 1.2 Isomer 2: 2.59 ± 0.7 |
| 5-di-tert-butoxycarbonyl-hydrazinocamptothecin | 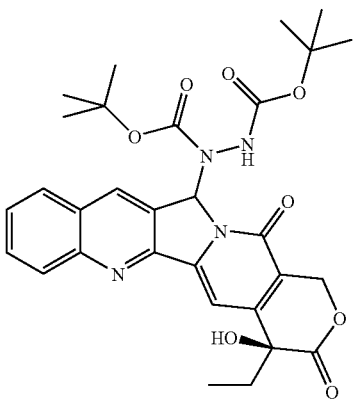 MW = 578.63 C30H34N4O8 | Isomer 1: 50 ± 16 Isomer 2: >100 |

-continued

| Name | Formula | NCI-H460 IC50 (µg/mL) Cell count |
|---|---|---|
| 5-NH2-camptothecin | 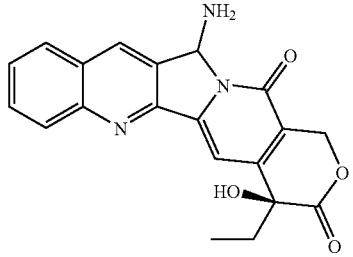 MW = 363.38 C20H17N3O4 | 11 ± 3.1 |
| 5-di-tert-butoxycarbonyl-hydrazinocamptothecin | 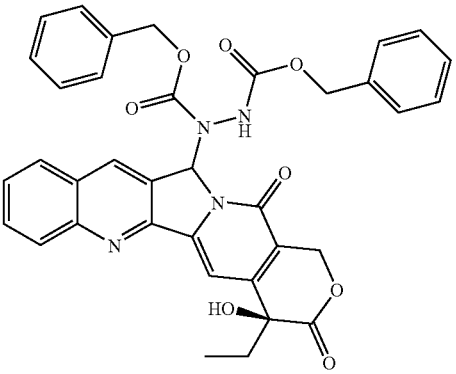 MW = 646.66 C36H30N4O8 | Isomers 1: 55 ± 15 Isomers 2: 39 ± 9.7 |

The most active compounds were evaluated in a DNA cleavage assay measuring the active concentration and damage persistence (see the section 'Examples'). The derivatives of formula (I) surprisingly show higher persistence in blocking DNA replication than the reference standards (particularly topotecan and camptothecin), while maintaining an effective cytotoxic activity.

In a further aspect, the invention relates to pharmaceutical compositions containing a compound of formula (I) together with pharmaceutically acceptable carriers and excipients. The pharmaceutical forms suitable to the oral or parenteral administration of the compounds (I) can be solid, preferably capsules, tablets and granules, or liquid, preferably injectable or infusion solutions.

The suitably formulated compounds of the invention can be used for the treatment of solid tumors and leukemias, in particular tumors of the lung, ovary, breast, stomach, liver, prostate, soft tissue sarcomas, head and neck, esophagus, pancreas, colon, rectum, glioblastoma, chronic and acute myelocytic leukemias.

EXAMPLES

Example I

20-OTES-camptothecin

Camptothecin (0.100 g, 0.287 mmols) is suspended in anhydrous dimethylformamide (3 mL), under inert atmosphere, and the resulting suspension is added with imidazole (0.980 g, 1.44 mmols). The mixture is stirred for 10' minutes, subsequently triethylsilyl chloride (TES-Cl) (0.193 mL, 1.15 mmols) is dropped therein, followed by addition of 4-dimethylamino pyridine (DMAP) (0.040 g 0.287 mmols). After 46 h, the reaction mixture is evaporated under vacuum, (TLC control of the complete disappearance of the reagent, eluent $CH_2Cl_2$/MeOH=30/1). The solid is subsequently redissolved in $CH_2Cl_2$ and washed with $H_2O$ and saturated $NH_4Cl$. The aqueous phase is extracted with $CH_2Cl_2$ (2×10 mL). The organic phases are combined and dried over $Na_2SO_4$, filtered and concentrated under vacuum, thereby obtaining the desired product (0.133 g, 0.287 mmols) as a pale yellow solid.

$^1$H NMR (CDCl$_3$, 400 MHz) δ 8.37 (s, 1H, Ar, H-7), 8.25 (d, 1H, J=8.4 Hz, Ar), 7.92 (d, 1H, J=8.0 Hz, Ar), 7.82 (t, 1H, J=8.0 Hz, Ar), 7.65 (t, 1H, J=8.4 Hz, Ar), 7.57 (s, 1H, H-14), 5.67 (d, 1H, J=16.4 Hz, H-17), 5.29 (s, 2H, H-5), 5.25 (d, 1H, J=16.4 Hz, H-17), 2.00-1.84 (m, 2H, H-19), 1.03-0.93 (m, 12H), 0.80-0.71 (m, 6H). $^{13}$C NMR (CDCl$_3$, 100 MHz) δ 171.7, 157.6, 152.5, 151.5, 149.0, 145.9, 130.9, 130.4, 130.0, 128.4, 128.1, 128.0, 127.9, 118.9, 94.4, 75.3, 66.0, 50.0, 33.2, 7.9, 7.2, 6.4.

Example II

20-OTES SN-38

SN-38 (0.100 g, 0.255 mmols) is suspended in anhydrous dimethylformamide (5 mL), under inert atmosphere and the resulting suspension is added with imidazole (0.087 g, 1.28 mmols). The mixture is stirred for 10' minutes, subsequently triethylsilyl chloride (TES-Cl), (0.171 mL, 1.02 mmols) is dropped therein, followed by addition of 4-dimethylamino pyridine (DMAP) (0.031 g, 0.255 mmols). After 52 h, the reaction mixture is evaporated under vacuum, monitoring by TLC ($CH_2Cl_2$/MeOH=10/1) the complete disappearance of the reagent. The solid is subsequently redissolved in $CH_2Cl_2$ and washed with $H_2O$ and saturated $NH_4Cl$. The aqueous phase is extracted with $CH_2Cl_2$ (2×10 mL). The organic phases are combined and dried over $Na_2SO_4$, filtered and concentrated under vacuum, thereby obtaining the desired product (0.121 g, 0.240 mmol, 94%) as a pale yellow solid.

$^1$H NMR ($CDCl_3$, 400 MHz) δ 9.26 (br s, 1H,OH), 8.14 (d, 1H, J=9.2 Hz, Ar, H-12), 7.58 (s, 1H, H-14), 7.49 (dd, 1H, $J_1$=9.2 Hz $J_1$=2.2 Hz, H-11), 7.46 (d, 1H, J=2.2 Hz, H-9), 5.70 (d, 1H, J=16.5 Hz, H-17), 5.28 (d, 1H, J=16.5 Hz, H-17), 5.23 (s, 2H, H-5), 3.05 (q, 2H, J=7.5 Hz), 1.97-1.81 (m, 2H, H-19), 1.32 (t, 3H, J=7.5 Hz, Me), 0.98-0.88 (m, 12H), 0.77-0.68 (m, 6H). $^{13}$C NMR ($CDCl_3$, 100 MHz) δ 172.1, 157.9, 156.6, 152.1, 149.0. 146.7, 144.6, 143.6, 131.9, 128.7, 126.9, 122.8, 117.9, 105.5, 98.5, 75.4, 65.9, 49.5, 32.9, 23.2, 13.5, 7.8, 7.2, 6.4.

Example III

10-OTBDMS-20-OTES SN-38

20-OTES SN-38 (0.121 g, 0.240 mmols) is dissolved in a $CH_2Cl_2$/THF=1:1 (8 mL) anhydrous mixture under inert atmosphere. Imidazole (0.081 g, 1.20 mmols) is added thereto followed, after 10' minutes, by tert-butyldimethylsilyl chloride (TBDMS-Cl), (0.144 mg, 0.957 mmols), then by 4-dimethylamino pyridine (DMAP), (0.029 g 0.240 mmols). After 18 h, the reaction mixture is evaporated under vacuum, monitoring by TLC (Hexane/AcOEt=1/1) the disappearance of the reagent. The solid is subsequently redissolved in $CH_2Cl_2$ and washed with $H_2O$ and saturated $NH_4Cl$. The aqueous phase is extracted with $CH_2Cl_2$ (2×10 mL) and the organic phases are combined, dried over $Na_2SO_4$, filtered and concentrated under vacuum. The residue is purified by flash chromatography ($SiO_2$, Hexane/AcOEt=1/1), thereby obtaining the desired product (0.127 g, 0.205 mmol, 85%) as a pale yellow solid.

$^1$H NMR ($CDCl_3$, 400 MHz) δ 8.14 (d, 1H, J=8.8 Hz, Ar, H-12), 7.49 (s, 1H, H-14), 7.40 (d, 1H, J=2.2 Hz, H-9), 7.38 (dd, 1H, $J_1$=8.8 Hz $J_2$=2.5 Hz, H-11) 5.67 (d, 1H, J=16.5 Hz, H-17), 5.25 (d, 1H, J=16.5 Hz, H-17), 5.23 (s, 2H, H-5), 3.11 (q, 2H, J=7.6 Hz), 1.99-1.82 (m, 2H, H-19), 1.38 (t, 3H, J=7.6 Hz, Me), 1.04 (s, 9H), 1.00-0.92 (m, 12H), 0.78-0.69 (m, 6H), 0.30 (s, 6H). $^{13}$C NMR ($CDCl_3$, 100 MHz) δ 171.9, 157 7, 155.1, 151.5, 150.1, 146.8, 145.6, 143.5, 132.2, 128.2, 126.9, 125.9, 118.0, 110.5, 97.7, 75.4, 66.0, 49.3, 33.2, 25.6, 23.1, 18.3, 13.7, 7.9, 7.2, 6.4, 4.3.

Example IV

20-OTES Topotecan

Topotecan (0.100 g, 0.238 mmols) is suspended in anhydrous dimethylformamide (5 mL), under inert atmosphere and the resulting suspension is added with imidazole (0.081 g, 1.19 mmols). The mixture is stirred for 10' minutes, subsequently triethyl silyl chloride (TES-Cl), (0.160 mL, 0.952 mmols) is dropped therein, followed by addition of 4-dimethylaminopyridine, (DMAP), (0.029 g 0.238 mmols). After 52 h, the reaction mixture is evaporated under vacuum, monitoring by TLC ($CH_2Cl_2$/MeOH=10/1) the complete disappearance of the reagent. The solid is subsequently redissolved in $CHCl_3$ and $H_2O$ and saturated $NH_4Cl$, the aqueous phase is extracted with $CHCl_3$ (2×15 mL). The organic phases are combined and dried over $Na_2SO_4$, filtered and concentrated under vacuum, thereby obtaining the desired product (0.120 g, 0.224 mmol, 94%) as a pale yellow solid.

$^1$H NMR ($CDCl_3$, 400 MHz) δ 9.65 (br s, 1H), 8.26 (s, 1H, Ar, H-7), 8.14 (d, 1H, J=8.8 Hz, Ar, H-12), 7.80 (d, 1H, J=8.8 Hz, Ar, H-11), 7.58 (s, 1H, H-14), 5.67 (d, 1H, J=16.5 Hz, H-17), 5.25 (d, 1H, J=16.5 Hz, H-17), 5.20 (s, 2H, H-5), 4.71 (s, 2H), 2.81 (s, 6H, 2 Me), 1.97-1.81 (m, 2H, H-19), 0.98-0.88 (m, 12H), 0.77-0.68 (m, 6H). $^{13}$C NMR ($CDCl_3$, 100 MHz) δ 172.1, 157.9, 156.6, 152.1, 150.8, 146.8, 144.3, 134.3, 131.2 129.9, 127.9, 123.0. 118.9, 110.1, 98.5, 75.4, 65.9, 51.1, 50.0. 43.1, 32.9, 7.8, 7.2, 6.4.

Example V

10-OTBDMS 20-OTES Topotecan

20-OTES Topotecan (0.120 g, 0.224 mmmols) is dissolved in a $CH_2Cl_2$/THF=1:1 anhydrous mixture (8 mL) under inert atmosphere. Imidazole (0.076 g, 1.12 mmols) is added followed, after 10' minutes, by tert-butyldimethylsilyl chloride (TBDMS-Cl), (0.135 mg, 0.896 mmols), then by 4-dimethylamino pyridine (DMAP), (0.027 g 0.224 mmols). After 21 h, the reaction mixture is evaporated under vacuum, monitoring by TLC (Hexane/AcOEt=1/1) the disappearance of the reagent. The solid is subsequently redissolved in $CHCl_3$ and $H_2O$ and saturated $NH_4Cl$, the aqueous phase is extracted with $CHCl_3$ (2×15 mL). The organic phases are combined and dried over $Na_2SO_4$, filtered and concentrated under vacuum. The residue is purified by flash chromatography ($SiO_2$, Hexane/AcOEt=1/1), thereby obtaining the desired product (0.116 g, 0.179 mmol, 80%) as a pale yellow solid.

$^1$H NMR ($CDCl_3$, 400 MHz) δ 8.26 (s, 1H, Ar, H-7), 8.14 (d, 1H, J=8.8 Hz, Ar, H-12), 7.81 (d, 1H, J=8.8 Hz, Ar, H-11), 7.59 (s, 1H, H-14), 5.64 (d, 1H, J=16.5 Hz, H-17), 5.22 (d, 1H, J=16.5 Hz, H-17), 5.19 (s, 2H, H-5), 4.71 (s, 2H), 2.81 (s, 6H, 2 Me), 1.97-1.81 (m, 2H, H-19), 1.04 (s, 9H), 0.98-0.88 (m, 12H), 0.77-0.68 (m, 6H), 0.30 (s, 6H). $^{13}$C NMR ($CDCl_3$, 100 MHz) δ 171.7, 157.7, 155.1, 151.5, 150.0. 146.8, 144.3, 134.3, 131.2 129.9, 127.9, 123.0. 118.9, 110.1, 98.5, 75.4, 65.9, 51.1, 50.0. 43.9, 32.9, 25.6, 18.3, 7.8, 7.2, 6.4, -4.3.

Example VI

Preparation of 20-OTES 10-hydroxycamptothecin

10-Hydroxycamptothecin (0.100 g, 0.275 mmols) is suspended in anhydrous dimethylformamide (5 mL), under inert atmosphere and the resulting suspension is added with imidazole (0.225 g, 3.31 mmols). The mixture is stirred for 10' minutes, subsequently triethylsilyl chloride (TES-Cl), (0.460 mL, 2,75 mmols) is dropped therein, followed by addition of 4-dimethylamino pyridine (DMAP) (0.068 g, 0.550 mmols). After 24 h the reaction mixture is evaporated under vacuum, monitoring by TLC the complete disappearance of the reagent ($CH_2Cl_2$/MeOH=20/1). The solid is subsequently redissolved in $CH_2Cl_2$ and washed with $H_2O$ and saturated $NH_4Cl$. The aqueous phase is extracted with $CH_2Cl_2$ (2×10 mL). The organic phases are combined, dried over $Na_2SO_4$, filtered and concentrated under vacuum, thereby obtaining the desired product (0.124 g, 0.259 mmol, 94%) as a pale yellow solid.

$^1$H NMR ($CDCl_3$+5% $CD_3OD$, 400 MHz) δ 8.10 (s, 1H, Ar, H-7), 8.05 (d, 1H, J=9.2 Hz, Ar), 7.50 (s, 1H, H-14), 7.39 (dd, 1H, $J_1$=9.2 Hz $J_2$=2.4 Hz, H-11), 7.11 (d, 1H, J=2.2 Hz, H-9), 5.60 (d, 1H, J=16.4 Hz, H-17), 5.21 (d, 1H, J=16.4 Hz, H-17), 5.15 (s, 2H, H-5), 1.97-1.81 (m, 2H, H-19), 0.98-0.88 (m, 12H), 0.76-0.68 (m, 6H). $^{13}$C NMR ($CDCl_3$+5% $CD_3OD$,

100 MHz) δ 172.2, 157.8, 156.7, 151.8, 149.2, 146.1, 144.1, 130.9, 129.8, 129.0, 128.6, 123.2, 117.8, 108.8, 98.1, 75.4, 65.8, 50.0, 32.9, 7.7, 7.1, 6.3.

Example VII

10-OTBDMS-20-OTES Camptothecin

10-Hydroxy-20-OTES-Camptothecin (0.105 g, 0.219 mmols) is dissolved in a $CH_2Cl_2/THF=1:1$ anhydrous mixture (4 mL) and under inert atmosphere. Imidazole (0.097 g, 1.42 mmols) is added followed, after 10' minutes, by tert-butyldimethylsilyl chloride (TBDMS-Cl), (0.164 mg, 1.10 mmols), then by 4-dimethylamino pyridine (DMAP) (0.040 g, 0.329 mmols). After 18 h, the reaction mixture is evaporated under vacuum, monitoring by TLC the complete disappearance of the reagent (Ciclohexane/AcOEt=1/3). The solid is subsequently redissolved in $CH_2Cl_2$ and washed with $H_2O$ and saturated $NH_4Cl$, the aqueous phase is extracted with $CH_2Cl_2$ (2×10 mL). The organic phases are combined, dried over $Na_2SO_4$, filtered and concentrated under vacuum. The residue is purified by flash chromatography ($SiO_2$, Ciclohexane/AcOEt=1/3), thereby obtaining the desired product (0.117 g, 0.197 mmol, 90%) as a pale yellow solid.

$^1$H NMR (CDCl$_3$, 400 MHz) δ 8.22 (s, 1H, Ar, H-7), 8.13 (d, 1H, J=9.2 Hz, Ar, H-12), 7.51 (s, 1H, H-14), 7.39 (dd, 1H, J$_1$=9.2 Hz J$_2$=2.8 Hz, H-11), 7.22 (d, 1H, J=2.8 Hz, H-9), 5.66 (d, 1H, J=16.5 Hz, H-17), 5.25 (s, 2H, H-5), 5.24 (d, 1H, J=16.5 Hz, H-17), 1.99-1.82 (m, 2H, H-19), 103 (s, 9H), 1.00-0.92 (m, 12H), 0.78-0.69 (m, 6H), 0.29 (s, 6H). $^{13}$C NMR (CDCl$_3$, 100 MHz) δ 172.0. 157.7, 155.1, 151.5, 150.6, 146.1, 145.1, 131.4, 129.4, 129.3, 128.7, 126.7, 118.3, 114.5, 97.7, 75.3, 66.0. 49.9, 33.1, 25.6, 18.3, 7.9, 7.2, 6.4, -4.3.

Example VIII

5-F-20-OTES-Camptothecin

Camptothecin 20-OTES (0.100 g, 0.216 mmols) is dissolved in anhydrous THF (6 mL) with stirring under inert atmosphere, then cooled to a temperature of −78° C. and a 1.0 M LiHMDS solution in THF (0.260 mL, 0.260 mmols) is dropped therein. After 20', NFSI (0.089 g, 0.281 mmols) in anhydrous THF (2 mL) is added. After 2 h at −78° C., temperature is left to raise to 25° C. and the disappearance of the reagent is monitored by TLC (Hexane/AcOEt=1/2). Formation of the two diastereomers is observed. After 3 h at room temperature, the reaction is quenched by addition of saturated $NH_4Cl$. The aqueous phase is extracted with $CH_2Cl_2$ (3×15 mL) and the organic phases are combined, dried over $Na_2SO_4$, filtered and concentrated under vacuum. The residue is purified by flash chromatography ($SiO_2$, Hexane/AcOEt=3/1, then 2/1 and finally 1/1), thereby obtaining a mixture of the two isomers (0.101 g, 0.210 mmol, 97%,) (1:1 isomers ratio) as a pale yellow solid. The two isomers are separated by further chromatography. In order of elution:

1$^{st}$ diastereomer: $^1$H NMR (CDCl$_3$, 400 MHz) δ 8.52 (s, 1H, Ar, H-7), 8.25 (d, 1H, J=8.4 Hz, Ar), 7.96 (d, 1H, J=8.4 Hz, Ar), 7.87 (t, 1H, J=8.4 Hz, Ar), 7.69 (t, 1H, J=8.4 Hz, Ar), 7.47 (d, 1H, $^1J_{HF}$=61.2 Hz, H-5), 7.45 (s, 1H, H-14), 5.62 (d, 1H, J=16.8 Hz, H-17), 5.22 (d, 1H, J=16.8 Hz, H-17), 2.02-1.84 (m, 2H, H-19), 1.03-0.93 (m, 12H), 0.80-0.71 (m, 6H). $^{13}$C NMR (CDCl$_3$, 100 MHz) δ 171.4, 157.5, 152.3, 151.1, 150.2 (d, J=1.5 Hz), 150.3 (d, J=1.5 Hz), 143.6 (d, J=5.3 Hz), 133.7, 131.7, 130.2, 128.9, 128.4, 127.9 (d, J=15.0 Hz), 126.3 (d, J=15.0 Hz), 121.8, 98.9, 93.8 (d, $^1J_{CF}$=213.2 Hz, C-5), 75.1, 65.7, 33.1, 7.8, 7.2, 6.4.

2$^{nd}$ diastereomer: $^1$H NMR (CDCl$_3$, 400 MHz) δ 8.51 (s, 1H, Ar, H-7), 8.25 (d, 1H, J=8.4 Hz, Ar), 7.96 (d, 1H, J=8.4 Hz, Ar), 7.87 (t, 1H, J=8.4 Hz, Ar), 7.68 (t, 1H, J=8.4 Hz, Ar), 7.51 (d, 1H, $^1J_{HF}$=60.8 Hz, H-5), 7.42 (s, 1H, H-14), 5.62 (d, 1H, J=17.2 Hz, H-17), 5.20 (d, 1H, J=17.2 Hz, H-17), 2.02-1.82 (m, 2H, H-19), 1.04-0.93 (m, 12H), 0.80-0.71 (m, 6H).$^{13}$C NMR (CDCl$_3$, 100 MHz) δ 171.2, 157.8, 152.5, 151.2, 150.3, 143.7, 133.7 (d, J=2.4 Hz), 131.7, 130.2, 128.9, 128.3, 127.9 (d, J=2.3 Hz), 126.3 (d, J=16.7 Hz), 121.8 (d, J=1.5 Hz), 99.0. 93.8 (d, $^1J_{CF}$=214.8 Hz, C-5), 75.0, 65.8, 33.3, 7.9, 7.1, 6.4.

Example IX

Preparation 5-F-camptothecin 1$^{st}$ diastereomer

The first diastereomer of 5-F-20-OTES-camptothecin (0.025 g, 0.052 mmols) is dissolved in anhydrous THF (5 mL) with stirring under inert atmosphere. Subsequently Et3N.3HF (0.060 mL, 0.368 mmols) is dropped therein. The reaction mixture is reacted for 28 h at room temperature, monitoring by TLC the disappearance of the reagent (Hexane/AcOEt=1/2). The solvent is evaporated off under vacuum and the residue is chromatographed ($SiO_2$, Hexane/AcOEt=1/1), thereby obtaining the desired product (0.019 g, 0.051 mmol, 98%) as a pale yellow solid.

$^1$H NMR (CDCl$_3$, 400 MHz) δ 8.52 (s, 1H, Ar, H-7), 8.25 (d, 1H, J=8.4 Hz, Ar), 7.96 (d, 1H, J=8.4 Hz, Ar), 7.87 (t, 1H, J=8.4 Hz, Ar), 7.69 (t, 1H, J=8.4 Hz, Ar), 7.59 (s, 1H, H-1 4), 7.46 (d, 1H, $^1J_{HF}$=61.2 Hz, H-5), 5.69 (d, 1H, J=16.8 Hz, H-17), 5.26 (d, 1H, J=16.8 Hz, H-17), 3.87 (br s, 1H, OH), 2.01-1.81 (m, 2H, H-19), 1.05 (t, 3H, J=7.6 Hz, Me). $^{13}$C NMR (CDCl$_3$, 100 MHz) δ 173.5, 157.6, 151.1, 151.0. 150.2, 144.1, 133.9, 131.9, 130.0. 129.0. 128.5, 127.8, 126.4, 121.7, 98.8, 93.8 (d, $^1J_{CF}$=214.0 Hz, C-5), 72.5, 66.0, 31.5, 7.8.

Example X

Preparation of 5-F-camptothecin $_2$nd diastereomer

The second diastereomer of 5-F-20-OTES-camptothecin (0.025 g, 0.052 mmols) is dissolved in anhydrous THF (5 mL) with stirring under inert atmosphere, subsequently Et3N.3HF (0.060 mL, 0.368 mmols) is dropped therein. The reaction mixture is reacted for 28 h at room temperature, monitoring by TLC the disappearance of the reagent (Hexane/AcOEt=1/2). The solvent is evaporated off under vacuum and the residue is chromatographed ($SiO_2$, Hexane/AcOEt=1/1), thereby obtaining the desired product (0.018 g, 0.050 mmol, 97%) as a pale yellow solid.

$^1$H NMR (CDCl$_3$, 400 MHz) δ 8.52 (s, 1H, Ar, H-7), 8.24 (d, 1H, J=8.4 Hz, Ar), 7.96 (d, 1H, J=8.4 Hz, Ar), 7.88 (t, 1H, J=8.4 Hz, Ar), 7.69 (t, 1H, J=8.4 Hz, Ar), 7.56 (s, 1H, H-14), 7.51 (d, 1H, $^1J_{HF}$=60.4 Hz, H-5), 5.69 (d, 1H, J=16.4 Hz, H-17), 5.25 (d, 1H, J=16.4 Hz, H-17), 3.87 (br s, 1H, OH), 1.98-1.78 (m, 2H, H-19), 1.04 (t, 3H, J=7.6 Hz, Me). $^{13}$C NMR (CDCl$_3$, 100 MHz) δ 173.3, 157.7, 151.2, 151.2, 150.2, 144.2, 133.8, 131.9, 130.0, 129.0, 128.5, 127.8, 126.4, 121.6, 98.9, 93.7 (d, $^1J_{CF}$=214.0 Hz, C-5), 72.5, 66.1, 31.6, 7.8.

Example XI

Preparation of 5-N3-20-OTES-camptothecin

Camptothecin 20-OTES (0.100 g, 0.216 mmols) is dissolved in anhydrous THF (6 mL) with stirring under inert atmosphere, then cooled to a temperature of −78° C. and a 1.0

M LiHMDS solution in THF (0.260 mL, 0.260 mmols) is dropped therein. After 20 min, tosyl azide (TsN$_3$) (0.055 g, 0.281 mmols) in anhydrous THF (2 mL) is added. After 2 h at −78° C., temperature is left to raise to 25° C. and the disappearance of the reagent is monitored by TLC (Hexane/AcOEt=2/1). Formation of the two diastereomers is observed. After 2 h 30 min at room temperature, the reaction is quenched by addition of saturated NH$_4$Cl. The aqueous phase is extracted with CH$_2$Cl$_2$ (3×15 mL) and the organic phases are combined, dried over Na$_2$SO$_4$, filtered and concentrated under vacuum. The residue, consisting of the two diastereomers, is purified by flash chromatography (SiO$_2$, Hexane/AcOEt=3/1, then 2/1 and finally 1/1), thereby obtaining (0.106 g, 0.210 mmol, 97%) of a mixture of the two isomers (ratio of the isomers 1:1) as a pale yellow solid. The two isomers are separated by further chromatography. In order of elution:

1$^{st}$ diastereomer: $^1$H NMR (CDCl$_3$, 400 MHz) δ 8.45 (s, 1H, Ar, H-7), 8.25 (d, 1H, J=8.4 Hz, Ar), 7.95 (d, 1H, J=8.4 Hz, Ar), 7.86 (t, 1H, J=8.4 Hz, Ar), 7.68 (t, 1H, J=8.4 Hz, Ar), 7.49 (s, 1H, H-14), 6.97 (s, 1H, H-5), 5.65 (d, 1H, J=16.8 Hz, H-17), 5.26 (d, 1H, J=16.8 Hz, H-17), 2.01-1.84 (m, 2H, H-19), 1.03-0.94 (m, 12H), 0.80-0.71 (m, 6H). $^{13}$C NMR (CDCl$_3$, 100 MHz) δ 171.6, 158.3, 152.2, 150.8, 150.0. 144.0. 132.9, 131.4, 130.1, 128.6, 128.3, 128.2, 128.1, 120.8, 98.7, 75.4, 75.2, 65.7, 33.1, 7.9, 7.2, 6.4.

2$^{nd}$ diastereomer: $^1$H NMR (CDCl$_3$, 400 MHz) δ 8.45 (s, 1H, Ar, H-7), 8.24 (d, 1H, J=8.4 Hz, Ar), 7.95 (d, 1H, J=8.4 Hz, Ar), 7.86 (t, 1H, J=8.4 Hz, Ar), 7.68 (t, 1H, J=8.4 Hz, Ar), 7.46 (s, 1H, H-14), 6.99 (s, 1H, H-5), 5.66 (d, 1H, J=16.8 Hz, H-17), 5.22 (d, 1H, J=16.8 Hz, H-17), 2.02-1.84 (m, 2H, H-19), 1.03-0.94 (m, 12H), 0.80-0.71 (m, 6H). $^{13}$C NMR (CDCl$_3$, 100 MHz) δ 171.4, 158.4, 152.3, 150.9, 150.0, 144.0, 132.9, 131.4, 130.1, 128.6, 128.3, 128.2, 128.1, 120.8, 98.7, 75.3, 75.1, 65.8, 33.3, 7.9, 7.2, 6.4.

Example XII

Preparation of 5-N3-camptothecin 1st diastereomer

The diastereomer 1 of 5-N3-20-OTES-camptothecin (0.070 g, 0.139 mmols) is dissolved in anhydrous THF (6 mL) with stirring under inert atmosphere, subsequently Et3N.3HF (0.170 mL, 1.016 mmols) is dropped therein. The reaction mixture is reacted for 26 h at room temperature, monitoring by TLC the disappearance of the reagent (Hexane/AcOEt=1/1). The solvent is evaporated off under vacuum and the residue is purified by flash chromatography (SiO$_2$, Hexane/AcOEt=1/1), thereby obtaining the desired product (0.053 g, 0.136 mmol, 98%) as a pale yellow solid.

$^1$H NMR (CDCl$_3$, 400 MHz) δ 8.44 (s, 1H, Ar, H-7), 8.24 (d, 1H, J=8.4 Hz, Ar), 7.93 (d, 1H, J=8.4 Hz, Ar), 7.85 (t, 1H, J=8.4 Hz, Ar), 7.67 (t, 1H, J=8.4 Hz, Ar), 7.63 (s, 1H, H-14), 6.97 (s, 1H, H-5), 5.70 (d, 1H, J=16.8 Hz, H-17), 5.29 (d, 1H, J=16.8 Hz, H-17), 3.99 (br s, 1H, OH), 2.00-1.84 (m, 2H, H-19), 1.04 (t, 3H, J=7.6 Hz, Me). $^{13}$C NMR (CDCl$_3$, 100 MHz) δ 173.6, 158.3, 150.8, 150.7, 149.8, 144.4, 133.1, 131.5, 129.9, 128.6, 128.3, 128.3, 128.1, 120.6, 98.6, 75.4, 72.7, 66.0, 31.5, 7.8.

Example XIII

Preparation of 5-N3-camptothecin 2$^{nd}$ diastereomer

The diastereomer 2 of 5-N3-20-OTES-camptothecin (0.055 g, 0.109 mmols) is dissolved in anhydrous THF (6 mL) with stirring under inert atmosphere, subsequently Et3N.3HF (0.135 mL, 0.820 mmols) is dropped therein. The reaction mixture is reacted for 26 h at room temperature, monitoring the disappearance of the starting reagent by TLC (Hexane/AcOEt=1/1). The solvent is evaporated off under vacuum and the residue is purified by flash chromatography (SiO$_2$, Hexane/AcOEt=1/1), thereby obtaining the desired product (0.042 g, 0.107 mmol, 98%) as a pale yellow solid.

$^1$H NMR (CDCl$_3$, 400 MHz) δ 8.45 (s, 1H, Ar, H-7), 8.23 (d, 1H, J=8.4 Hz, Ar), 7.95 (d, 1H, J=8.4 Hz, Ar), 7.85 (t, 1H, J=8.4 Hz, Ar), 7.68 (t, 1H, J=8.4 Hz, Ar), 7.60 (s, 1H, H-14), 7.00 (s, 1H, H-5), 5.74 (d, 1H, J=16.8 Hz, H-17), 5.28 (d, 1H, J=16.8 Hz, H-17), 3.86 (br s, 1H, OH), 1.98-1.82 (m, 2H, H-19), 1.04 (t, 3H, J=7.6 Hz, Me). $^{13}$C NMR (CDCl$_3$, 100 MHz) δ 173.4, 158.4, 150.9, 150.7, 149.8, 144.5, 133.0, 131.5, 129.9, 128.6, 128.4, 128.3, 128.1, 120.6, 98.6, 75.3, 72.6, 66.1, 31.6, 7.8.

Example XIV

Preparation of 5-NH$_2$-camptothecin

The diastereomer 2 of 5-N3-20-OH-camptothecin (0.050 g, 0.129 mmols) is dissolved in a mixture of anhydrous THF (1.5 mL) and anhydrous MeOH (6 mL) with stirring under inert atmosphere, subsequently is added with Pd/C (14 mg~10%) and two cycles in vacuo/H$_2$ (H$_2$ balloon pressure) are carried out. The reaction mixture is reacted for 3 h at room temperature monitoring by TLC (Hexane/AcOEt=1/3) the disappearance of the reagent, then filtered through Celite and washed with CH$_2$Cl$_2$ (2×15 mL). The solvent is evaporated off under vacuum. $^1$H NMR spectroscopy of the reaction crude reveals the presence of the desired product as a 1:1 mixture of two epimers at the C5 position. Flash chromatography (SiO$_2$, CH$_2$Cl$_2$/MeOH=35/1 then 25/1) allows to recovery the mixture of the two diastereomers (0.046 g, 0.126 mmol, 98%).

$^1$H NMR (CDCl$_3$, 400 MHz) δ 8.48 (s, 1H, Ar, H-7), 8.22-8.17 (m, 1H, Ar), 7.95-7.90 (m, 1H, Ar), 7.85-7.78 (m, 1H, Ar), 7.68-7.60 (m, 1H, Ar), 7.58 (s, 0.5H, H-14), 7.54 (s, 0.5H, H-14) 6.50 (s, 0.5H, H-5), 6.47 (s, 0.5H, H-5), 5.74-5.64 (m, 1H, H-17), 5.28-5.22 (m, 1H, H-17), 4.00-2.40 (br s, 3H, OH+NH$_2$), 1.98-1.82 (m, 2H, H-19), 1.07-1.01 (m, 3H, Me). $^{13}$C NMR (CDCl$_3$, 100 MHz) δ 173.8 (2C), 158.5 (2C), 151.2 (2C), 150.4 (2C), 149.7 (2C), 144.5 (2C), 132.7 (2C), 131.0 (2C), 129.8 (2C), 128.5 (2C), 128.3 (2C), 128.0 (2C), 127.8 (2C), 120.2 (2C), 113.8 (2C), 97.7 (2C), 72.7 (2 C), 66.3, 66.0, 31.5 (2C), 7.8, 7.8.

Example XV 5-di-t-Butoxycarbonylhydrazino-20-OTES-camptothecin

Camptothecin 20-OTES (0.100 g, 0.216 mmols) is dissolved in anhydrous THF (6 mL) with stirring under inert atmosphere, then cooled to a temperature of −78° C. and a 1.0 M LiHMDS solution in THF (0.281 mL, 0.281 mmols) is dropped therein. After 20', di-tert-butylazo dicarboxylate (DTBAC) (0.075 g, 0.324 mmols) in anhydrous THF (2 mL) is added. After 4 h at −78° C., the disappearance of the reagent is monitored by TLC (Hexane/AcOEt=3/1). Formation of the two diastereomers is observed. The reaction is quenched by addition of saturated NH$_4$Cl. The aqueous phase is extracted with CH$_2$Cl$_2$ (3×15 mL) and the organic phases are combined, dried over Na$_2$SO$_4$, filtered and concentrated under vacuum. The residue is purified by flash chromatography (SiO$_2$, Hexane/AcOEt=3/1), thereby obtaining a mixture of the two isomers (0.145 g, 0.210 mmol, 97%). The two isomers are separated by further chromatography. In order of elution:

1$^{st}$ diastereomer: $^1$H NMR (CDCl$_3$, 400 MHz) δ 8.80 (br s, 1H, Ar), 8.23 (d, 1H, J=8.4 Hz, Ar), 8.01 (br d, 1H, Ar), 7.90-7.71 (m, 2H, Ar), 7.70-7.45 (m, 2H, Ar +H-14), 6.52 (br s, 1H, H-5), 5.61 (d, 1H, J=16.8 Hz, H-17), 5.23 (d, 1H, J=16.8 Hz, H-17), 2.03–1.81 (m, 2H, H-19), 1.79-1.08 (br s, 18 H), 1.06-0.92 (m, 12H), 0.80-0.70 (m, 6H). $^{13}$C NMR (CDCl$_3$, 100 MHz) δ 171.7, 157.8, 155.5, 155.5, 152.0, 152.0, 151.2, 149.4, 145.0, 132.1, 130.6, 130.0, 128.7, 128.4, 127.9, 119.9, 98.2, 82.7, 81.5, 79.7, 75.2, 65.7, 33.2, 28.3, 27.6, 7.7, 7.2, 6.4.

$_2$nd diastereomer: $^1$H NMR (CDCl$_3$, 400 MHz) δ 8.79 (br s,1H, Ar), 8.23 (d, 1H, J=8.4 Hz, Ar), 8.01 (br d, 1H, Ar), 7.85-7.76 (m, 2H, Ar), 7.65 (br t, 1H, J=8.4 Hz, Ar), 7.52 (s, 1H, H-14), 6.54 (br s, 1H, H-5), 5.61 (d, 1H, J=16.8 Hz, H-17), 5.22 (d, 1H, J=16.8 Hz, H-17), 2.03-1.82 (m, 2H, H-19), 1.76-1.08 (br s, 18H), 1.04-0.92 (m, 12H), 0.80-0.70 (m, 6H). $^{13}$C NMR (CDCl$_3$, 100 MHz) δ 171.5, 157.9, 155.5, 155.5, 152.3, 152.0. 151.2, 149.4, 145.1, 132.1, 130.6, 130.0, 128.7, 128.4, 127.9, 119.9, 98.2, 82.9, 81.5, 79.6, 75.2, 65.8, 33.3, 28.3, 27.4, 7.8, 7.2, 6.4.

Example XVI

Preparation of 5-di-t-butoxycarbonylhydrazino-camptothecin 1$^{st}$ diastereomer 5-di-t-Butoxycarbonylhydrazino-20-OTES-camptothecin (0.050 g, 0.072 mmols) first diastereomer is dissolved in anhydrous THF (4 mL) with stirring under inert atmosphere, subsequently Et$_3$N.3HF (0.088 mL, 0.542 mmols) is dropped therein. The reaction mixture is reacted for 35 h at room temperature, monitoring by TLC the disappearance of the reagent (Hexane/AcOEt=3/2). The solvent is evaporated off under vacuum and the residue is purified by flash chromatography (SiO$_2$, Hexane/AcOEt=3/2), thereby obtaining the desired compound (0.041 g, 0.071 mmol, 98%) as a pale yellow solid.

The product is further purified by crystallization from CH$_2$Cl$_2$/Pentane=1/50.

$^1$H NMR (CDCl$_3$, 400 MHz) δ 8.77 (br s, 1H, Ar), 8.16 (br d, 1H, J=8.0 Hz, Ar), 7.97 (br s, 1H, Ar), 7.86-7.50 (m, 4H, Ar), 6.51 (br s, 1H, H-5), 5.66 (d, 1H, J=16.4 Hz, H-17), 5.24 (d, 1H, J=16.4 Hz, H-17), 3.86 (br s, 1H, OH), 2.00-1.80 (m, 2H, H-19), 1.79-1.13 (br s, 18H), 1.03 (t, 3H, J=7.6 Hz, Me). $^{13}$C NMR (CDCl$_3$, 100 MHz) δ 173.7, 157.9, 155.5, 155.5, 152.1, 151.3, 150.7, 149.6, 145.7, 132.3, 130.7, 129.9, 128.7, 127.9, 127.6, 120.0, 97.9, 82.8, 81.6, 79.7, 72.7, 66.1, 31.8, 28.3, 27.7, 7.7.

Example XVII

Preparation of 5-di-t-butoxycarbonylhydrazino-camptothecin 2$^{nd}$ diastereomer 5-di-t-Butoxycarbonylhydrazino-20-OTES-camptothecin (0.050 g, 0.072 mmols) 2$^{nd}$ diastereomer is dissolved in anhydrous THF (4.5 mL) with stirring under inert atmosphere, subsequently Et$_3$N.3HF (0.088 mL, 0.542 mmols) is dropped therein. The reaction mixture is reacted for 35 h at room temperature, monitoring by TLC the disappearance of the reagent (Hexane/AcOEt=3/2). The solvent is evaporated off under vacuum and the residue is purified by flash chromatography (SiO$_2$, Hexane/AcOEt=3/2), thereby obtaining the desired compound (0.040 g, 0.069 mmol, 96%) as a pale yellow solid. The product is further purified by crystallization from CH$_2$Cl$_2$/Pentane=1/50.

$^1$H NMR (CDCl$_3$, 400 MHz) δ 8.79 (br s, 1H, Ar), 8.22 (br d, 1H, J=8.4 Hz, Ar), 7.99 (br s, 1H, Ar), 7.88-7.50 (m, 4H, Ar), 6.53 (br s, 1H, H-5), 5.65 (d, 1H, J=16.4 Hz, H-17), 5.26 (d, 1H, J=16.4 Hz, H-17), 3.80 (br s, 1H, OH), 2.00-1.80 (m, 2H, H-19), 1.79-1.13 (br s, 18H), 1.03 (t, 3H, J=7.2 Hz, Me). $^{13}$C NMR (CDCl$_3$, 100 MHz) δ 173.6, 157.9, 155.4, 155.4, 152.1, 151.3, 150.8, 149.5, 145.6, 132.3, 130.8, 129.8, 128.7, 127.9, 127.8, 119.8, 98.0, 83.0, 81.5, 79.7, 72.7, 66.3, 31.8, 28.3, 27.7, 7.8.

Example XVIII

Preparation of 5-dibenzyloxycarbonylhydrazino-20-OTES-camptothecin

Camptothecin 20-OTES (0.100 g, 0.216 mmols) is dissolved in anhydrous THF (6 mL) with stirring under inert atmosphere, then cooled to a temperature of −78° C. and a 1.0 M LiHMDS solution in THF (0.281 mL, 0.281 mmols) is dropped therein. After 20', dibenzyl azodicarboxylate (0.097 g, 0.324 mmols) in anhydrous THF (2 mL) is added. After 3 h at −78° C., temperature is left to raise to 25° C. and the disappearance of the reagent is monitored by TLC (Hexane/AcOEt=3/1). Formation of the two diastereomers is observed. After 90 min at room temperature, the reaction is quenched by addition of saturated NH$_4$Cl. The aqueous phase is extracted with CH$_2$Cl$_2$ (3×15 mL) and the organic phases are combined, dried over Na$_2$SO$_4$, filtered and concentrated under vacuum. The residue is purified by flash chromatography (SiO$_2$, Hexane/AcOEt=4/1 then 7/2), thereby obtaining a pale yellow solid (0.161 g, 0.212 mmol, 98%). The two isomers are separated by further chromatography. In order of elution:

1$^{st}$ diastereomer: $^1$H NMR (CDCl$_3$, 400 MHz) δ 8.70 (br s, 1H, Ar), 8.39 (br s 1H, Ar), 8.22 (br d, 1H, J=7.6 Hz, Ar), 7.95 (br d, 1H, J=7.6 Hz, Ar), 7.83 (br t, 1H, J=7.6 Hz, Ar), 7.65 (br t, 1H, J=7.6 Hz, Ar), 7.64-7.00 (m, 11H, Ar +H-14), 6.49 (br s, 1H, H-5), 5.57 (d, 1H, J=16.4 Hz, H-17), 5.47-4.44 (m, 5H), 1.98-1.82 (m, 2H, H-19), 1.02-0.89 (m, 12H), 0.80-0.70 (m, 6H). $^{13}$C NMR (CDCl$_3$, 100 MHz) δ 171.6, 158.0. 156.3, 156.3, 153.0, 152.2, 151.0, 149.6, 144.8, 135.3, 132.1, 130.6, 130.0, 128.6-127.8 (11C), 119.9, 98.4, 79.5, 75.2, 68.4, 67.9, 65.6, 33.0. 7.9, 7.2, 6.4.

2$^{nd}$ diastereomer: $^1$H NMR (CDCl$_3$, 400 MHz) δ 8.85 (br s, 1H, Ar), 8.58 (br s 1H, Ar), 8.20 (br s, 1H, Ar), 7.93 (br s, Ar), 7.81 (br t, 1H, J=7.6 Hz, Ar), 7.63 (br t, 1H, J=7.6 Hz, Ar), 7.56-6.90 (m, 11H, Ar +H-14), 6.52 (br s, 1H, H-5), 5.55 (d, 1H, J=16.8 Hz, H-17), 5.44-4.71 (m, 5H), 1.98-1.80 (m, 2H, H-19), 1.05-0.90 (m, 12H), 0.81-0.70 (m, 6H). $^{13}$C NMR (CDCl$_3$, 100 MHz) δ 171.5, 157.9, 156.4, 156.4, 152.9, 152.4, 150.9, 149.4, 144.8, 135.3, 132.1, 130.6, 129.9, 128.6-127.8 (11C), 119.9, 98.5, 79.3, 75.2, 68.4, 67.8, 65.6, 32.9, 7.8, 7.2, 6.4.

Example XIX

Preparation of 5-dibenzyloxycarbonylhydrazino-camptothecin 1$^{st}$ diastereomer 5-Dibenzyloxycarbonylhydrazino-20-OTES-camptothecin 1$^{st}$ diastereomer (0.140 g, 0.184 mmols) is dissolved in anhydrous THF (6 mL) with stirring under inert atmosphere, subsequently Et₃N.3HF (0.225 mL, 1.380 mmols) is dropped therein. The reaction mixture is reacted for 52 h at room temperature, monitoring by TLC the disappearance of the reagent (Hexane/AcOEt=1/3). The solvent is evaporated off under vacuum and the residue is purified by flash chromatography (SiO$_2$, Hexane/AcOEt=1/1 then 2/3), thereby obtaining (0.113 g, 0.175 mmol, 95%) as a pale yellow solid. The product is further purified by crystallization from CH$_2$Cl$_2$/Pentane=1/50.

$^1$H NMR (CDCl$_3$, 400 MHz) δ 8.67 (br s, 1H, Ar), 8.39 (br s 1H, Ar), 8.12 (br d, 1H, J=7.6 Hz, Ar), 7.95 (br s, 1H, Ar), 7.74 (br t, 1H, J=7.6 Hz, Ar), 7.65-6.66 (m, 12H, Ar+H-14), 6.48 (br s, 1H, H-5), 5.55 (d, 1H, J=16.0 Hz, H-17), 5.42-4.44 (m, 5H), 3.86 (br s, 1H, OH), 1.92-1.72 (m, 2H, H-19), 0.95 (t, 3H, J=7.6 Hz, Me). $^{13}$C NMR (CDCl$_3$, 100 MHz) δ 173.5, 158.0, 156.2, 156.0, 153.0, 150.9, 150.9, 149.5, 145.3, 135.4, 132.2, 130.7, 129.8, 128.7-127.8 (11 C), 119.9, 98.2, 79.6, 72.7, 68.5, 68.0, 65.9, 31.6, 7.8.

Example XX

Preparation of 5-dibenzyloxycarbonylhydrazino-camptothecin 2$^{nd}$ diastereomer 5-Dibenzyloxycarbonylhydrazino-20-OTES-camptothecin 2$^{nd}$ diastereomer (0.140 g, 0.184 mmols) is dissolved in anhydrous THF (6 mL) with stirring under inert atmosphere, subsequently Et₃N.3HF (0.150 mL, 0.921 mmols) is dropped therein. The reaction mixture is reacted for 55 h at room temperature, monitoring by TLC the disappearance of the reagent (Hexane/AcOEt=3/2). The solvent is evaporated off under vacuum and the residue is purified by flash chromatography (SiO$_2$, Hexane/AcOEt=1/1), thereby obtaining the desired compound (0.113 g, 0.175 mmol, 95%) as a pale yellow solid. The product is further purified by crystallization from CH$_2$Cl$_2$/Pentane=1/50.

$^1$H NMR (CDCl$_3$, 400 MHz) δ 8.71 (br s, 1H, Ar), 8.34 (br s 1H, Ar), 8.18 (br s, 1H, Ar), 7.94 (br s, 1H, Ar), 7.79 (br t, 1H, J=7.6 Hz, Ar), 7.70-6.70 (m, 12H, Ar+H-14), 6.52 (br s, 1H, H-5), 5.53 (d, 1H, J=16.4 Hz H-17), 5.44-4.48 (m, 5H), 3.87 (br s, 1H, OH), 1.90-1.70 (m, 2H, H-19), 0.99 (t, 3H, J=7.6 Hz, Me). $^{13}$C NMR (CDCl$_3$, 100 MHz) δ 173.4, 158.0, 156.3, 156.1, 153.0, 151.0, 150.9, 149.6, 145.3, 135.5, 132.3, 130.8, 129.8, 128.7-127.8 (11 C), 119.8, 98.4, 79.5, 72.7, 68.5, 67.8, 66.0. 31.6, 7.7.

Example XXI

Cell Growth Inhibition Assay

H460 Cells from human large cell lung tumor were cultured in RPMI-1640 medium containing 10% foetal calf serum. Cell sensitivity was determined by cell growth inhibition assay after 1 or 72 hr drug exposure. The cells in logarithmic growth were collected and seeded in duplicate in 6-wells plates. Twenty-four hours after seeding, cells were exposed to the drugs and counted with a Coulter conter 72 hours after exposure to the drugs for the determination of IC$_{50}$s. IC$_{50}$ is defined as the concentration inhibiting by 50% cell growth compared with untreated controls growth.

Example XXII

Topoisomerase-I—Dependent DNA Rupture Assay

DNA ruptures were determined using a 751-bp BamHI-EcoRI DNA SV40 purified gel (Beretta G L, Binaschi M, Zagni AND, Capuani L, Capranico G. Tethering a type IB topoisomerase to a DNA site by enzyme fusion to a heterologous site-selective DNA-binding protein domain. Cancer Res 1999; 59:3689-97). DNA fragments were only labeled at 3'. The DNA rupture reaction (20,000 cpm/sample) was carried out in 20 ml of 10 mM Tris-HCL (pH 7.6), 150 mM KCl, 5 mM MgCl$_2$, 15 μg/mL BSA, 0.1 mM thiothreitol, and the human recombinant enzyme (full length top1) for 30 min at 37° C. The reactions were blocked using 0.5% SDS and 0.3 mg/mL K proteinase for 45 min. at 42° C. DNA damage persistence was tested at different times adding 0.6 M NaCl after 30 min. incubation with 10 μM of the drug. After precipitation, DNA was resuspended in denaturation buffer (80% formamide, 10 mM NaOH, 0.01 M EDTA and 1 mg/mL dye) before seeding in denaturating gel (7% polyacrylamide in TBE buffer). All of DNA rupture levels were measured by means of a Phospholmager model 425 (Molecular Dynamics) (Dallavalle S, Ferrari A, Biasotti B, et al. Novel 7-oxyiminomethyl camptothecin derivatives with potent in vitro and in vivo antitumor activity. J Med Chem 2001; 44:3264-74).

Persistence of DNA Damage (%)

| Compounds | Time (min) | | | |
|---|---|---|---|---|
| | 0 | 1 | 5 | 10 |
| Topotecan | 100 | 65 | 20 | 10 |
| Camptothecin | 100 | 58 | 23 | 20 |
| SN38 | 100 | 60 | 33 | 28 |
| 5-F CPT isomers 1 | 100 | 18 | 18 | 10 |
| 5-F CPT isomers 2 | 100 | 10 | 10 | 13 |
| 5-N3 CPT | 100 | 50 | 30 | 15 |

The invention claimed is:
1. Compounds of general formula I:

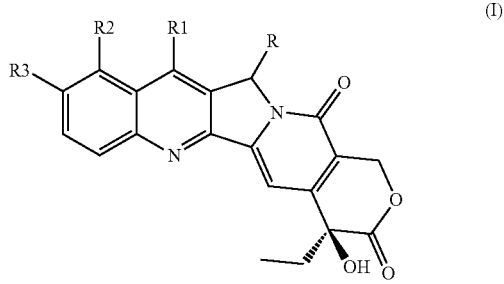

wherein:
R is F, Cl, Br, I, —N3, —COOR', —CONR'R", or —NHR'"—NR'R", in which R', R" and R'" are each independently H, alkyl, aryl, arylalkyl, acyl, alkoxycarbonyl, or aryloxycarbonyl;
R1 is hydrogen, alkyl, aminoalkyl, hydroxyalkyl, nitrile, alkoxymino, aryloxymino, or silylalkyl;
R2 is hydrogen, hydroxyl, alkoxy, or aminoalkyl;
R3 is hydrogen, optionally protected hydroxyl, alkoxy, or aminoalkyl;
wherein the alkyl, acyl, alkoxy, aminoalkyl or alkoxymino groups contain 1 to 8, carbon atoms, in a straight or branched chain, and the aryl and aryloxy groups contain 5 to 10 carbon atoms; and the pharmaceutically acceptable salts, isomers, enantiomers, diastereomers thereof and corresponding mixtures.

2. A compound of formula (I) as claimed in claim 1, which is selected from the group consisting of:
a) 5-F-camptothecin;
b) 5-N3-camptothecin;
c) 5-di-tertbutoxycarbonylhydrazinocamptothecin; and
d) 5-di-benzyloxycarbonylhydrazinocamptothecin.

3. A process for the preparation of compounds of formula (I), comprising the steps shown in the following Scheme, wherein:
a) one or more hydroxy groups are protected;
b) a carbanion is formed at position 5 and reacted with an electrophilic reagent; and
c) the protection of the hydroxy groups is removed;

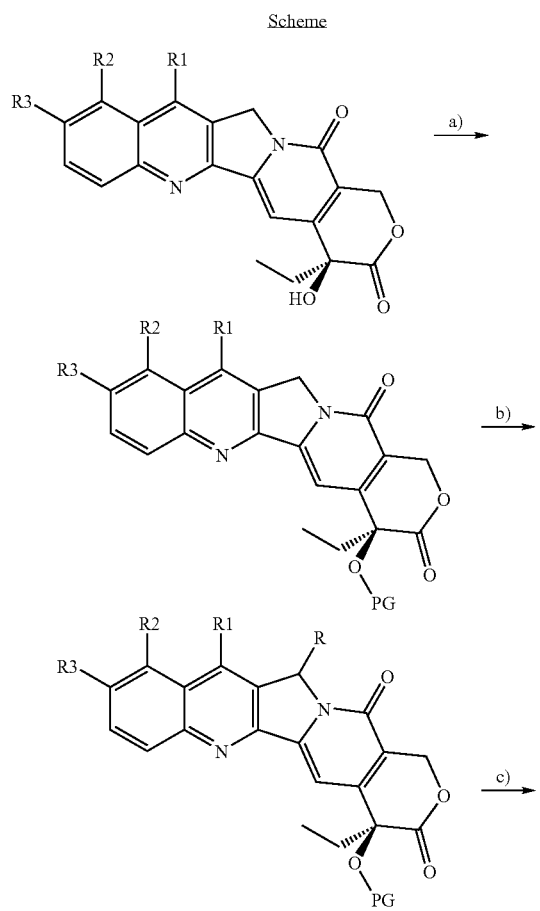

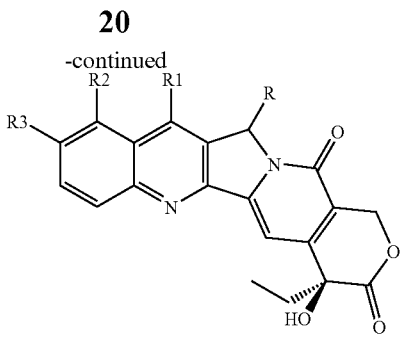

wherein:
R is F, Cl, Br, I, —N3, —COOR', —CONR'R", —NHR'''—NR'R" in which R', R" and R''' are each independently H, alkyl, aryl, arylalkyl, acyl, alkoxycarbonyl, or aryloxycarbonyl;
R1 is hydrogen, alkyl, aminoalkyl, hydroxyalkyl, nitrile, alkoxymino, aryloxymino, or silylalkyl;
R2 is hydrogen, hydroxyl, alkoxy, or aminoalkyl;
R3 is hydrogen, optionally protected hydroxyl, alkoxy, or aminoalkyl;
wherein the alkyl, acyl, alkoxy, aminoalkyl or alkoxymino groups contain 1 to 8 carbon atoms, in a straight or branched chain, and the aryl and aryloxy groups contain 5 to 10 carbon atoms;
PG is an OH-protecting group; and
the pharmaceutically acceptable salts, isomers enantiomers, diastereomers thereof and corresponding mixtures.

4. A pharmaceutical composition containing a compound of formula (I) of claim 1 together with one or more pharmaceutically acceptable carriers and excipients.

5. A pharmaceutical composition as claimed in claim 4, which is in a form suited to oral or parenteral administration.

6. A method for the treatment of tumors, comprising administering an effective amount of a compound of claim 1 to a person in need thereof.

7. The method of claim 6, wherein said tumors are solid tumors or leukemias.

8. A method for the treatment of tumors, comprising administering an effective amount of the pharmaceutical composition of claim 4 to a person in need thereof.

9. The method of claim 8, wherein said tumors are solid tumors or leukemias.

10. The method of claim 7, wherein said tumors are tumors of the lung, ovary, breast, stomach, liver, prostate, esophagus, pancreas, head, or neck, soft tissues sarcomas, glioblastoma, or chronic or acute myelocytic leukemias.

11. The method of claim 9, wherein said tumors are tumors of the lung, ovary, breast, stomach, liver, prostate, esophagus, pancreas, head, or neck, soft tissues sarcomas, glioblastoma, or chronic or acute myelocytic leukemias.

* * * * *